United States Patent
Hinarejos Esteve et al.

(10) Patent No.: US 9,686,999 B2
(45) Date of Patent: Jun. 27, 2017

(54) STRAIN OF BACILLUS SUBTILIS FOR COMBATING PLANT DISEASES

(75) Inventors: Estefania Hinarejos Esteve, Valencia (ES); Raquel Del Val Buedo, Valencia (ES); Nuria Tarancon Valera, Valencia (ES); Enríque Riquelme Terres, Valencia (ES)

(73) Assignee: INVESTIGACIONES Y APLICACIONES BIOTECHNOLOGICAS, S.L., Moncada (Valencia) (ES)

( * ) Notice: Subject to any disclaimer, the term of this patent is extended or adjusted under 35 U.S.C. 154(b) by 0 days.

(21) Appl. No.: 14/352,433

(22) PCT Filed: May 4, 2012

(86) PCT No.: PCT/ES2012/070310
§ 371 (c)(1),
(2), (4) Date: Jun. 23, 2014

(87) PCT Pub. No.: WO2013/060910
PCT Pub. Date: May 2, 2013

(65) Prior Publication Data
US 2014/0314718 A1    Oct. 23, 2014

(30) Foreign Application Priority Data
Oct. 28, 2011   (ES) .................................. 201131743

(51) Int. Cl.
*A01N 63/00*   (2006.01)
*A01N 63/02*   (2006.01)
*C12R 1/125*   (2006.01)

(52) U.S. Cl.
CPC ............. *A01N 63/02* (2013.01); *A01N 63/00* (2013.01); *C12R 1/125* (2013.01)

(58) Field of Classification Search
CPC ........ A01N 63/00; A01N 63/02; A01N 25/00; C12Q 1/6895; C12Q 2600/158; C12R 1/125; C12N 1/20
See application file for complete search history.

(56) References Cited

U.S. PATENT DOCUMENTS

2008/0152684 A1    6/2008 Tzeng et al.

FOREIGN PATENT DOCUMENTS

| WO | 98/21964 | 5/1998 |
|---|---|---|
| WO | 98/50422 | 11/1998 |
| WO | 00/29426 | 5/2000 |

OTHER PUBLICATIONS

Nalisha et al., Malaysian Journal of Microbiology, 2006; 2(2): 19-23.*
Torsten Stein, "Bacillus subtilis antibiotics: structures, syntheses and specific functions," Molecular Microbiology, 2005, vol. 56, No. 4, pp. 845-857.
Serenade Max, A Wettable Powder Biofungicide: For Agricultural Use, XP007917125, AgraQuest, Inc., 2009, pp. 1-17.
International Search Report issued Aug. 31, 2012 in International (PCT) Application No. PCT/ES2012/070310.

* cited by examiner

*Primary Examiner* — Debbie K Ware
(74) *Attorney, Agent, or Firm* — Wenderoth, Lind & Ponack, L.L.P.

(57) ABSTRACT

The present invention relates to an isolated strain of *Bacillus subtilis* (IAB/BS/03) deposited at the DSM German Type Culture Collection under Access No DSM 24682, or a mutant of said strain, and also deposited at the Spanish type culture collection under Access number CECT 7254, the property of the company filing the patent, in which said strain and/or the mutant thereof exhibits antifungal and antibacterial activity, with a profile of action different from that of other strains of *Bacillus subtilis* and with much greater potency in terms of the capacity thereof to act as a field biological control agent. The invention also includes methods for preventing and treating fungal and bacterial diseases in plants using said bacterial strains or supernatants containing antibiotics or pure antibiotics obtained from said bacterial strains, in which said antibiotics are contained in a composition.

9 Claims, 15 Drawing Sheets

| Pest Code | | | BREMLA | BREMLA | BREMLA | BREMLA | BREMLA |
|---|---|---|---|---|---|---|---|
| Crop Code | | | LACSR | LACSR | LACSR | LACSR | LACSR |
| Description | | | Fresh market | Fresh market | Fresh market | Fresh market | Fresh market |
| Part Rated | | | LEAF C | LEAF C | LEAF C | LEAF C | LEAF - |
| Rating Date | | | 28/3/2011 | 4/4/2011 | 18/4/2011 | 18/4/2011 | 3/5/2011 |
| Rating Type | | | PESSEV | PESSEV | PESSEV | PESSEV | PESSEV |
| Rating Unit | | | %AREA | %AREA | %AREA | %AREA | %AREA |
| Sample Size, Unit | | | 40 PLANT | 40 PLANT | 40 PLANT | 40 PLANT | 40 PLANT |
| Collection Basis, Unit | | | 100 LEAF | 100 LEAF | 100 LEAF | 100 LEAF | 100 LEAF |
| Footnote Number | | | 1 | 1 | 1 | 1 | 1 |
| Trt-Eval Interval | | | 7 DA-A | 7 DA-B | 14 DA-C | 14 DA-C | 29 DA-C |
| ARM Action Codes | | | | S05 | | TL[3] S05 | S05 |
| Trt Treatment | Rate | Appl | | | | | |
| No. Name | Rate Unit | Code | 1 | 2 | 3 | 4 | 5 |
| 1 Untreated Check | | | 0.1 | 0.8 a | 6.2 | 3.3 a | 53.9 a |
| 2 Bacillus subtilis strain IABBS03 | 100 g/100 l | ABC | 0.0 | 0.3 b | 0.7 | 0.3 c | 19.0 b |
| 3 Bacillus subtilis strain IABBS03 | 150 g/100 l | ABC | 0.0 | 0.2 b | 0.6 | 0.2 c | 10.8 b |
| 4 Bacillus subtilis strain IABBS03 | 200 g/100 l | ABC | 0.0 | 0.2 b | 0.9 | 0.3 c | 16.8 b |
| 5 CURZATE M Reference chemical | 300 g/100 l | ABC | 0.0 | 0.1 b | 0.7 | 0.2 c | 14.2 b |
| 6 SERENADE MAX (QST 713) | 600 g/100 l | ABC | 0.0 | 0.1 b | 2.0 | 0.8 b | 14.8 b |
| LSD (P=Various) | | | 0.07 | 0.37 | 1.10 | 0.09t | 10.08 |
| Standard Deviation | | | 0.05 | 0.25 | 0.73 | 0.06t | 6.69 |
| CV | | | 312.69 | 85.0 | 39.37 | 27.28 | 30.99 |
| Grand Mean | | | 0.02 | 0.29 | 1.86 | 0.21t | 21.58 |
| Bartlett's X2 | | | 0.0 | 3.163 | 22.842 | 10.792 | 2.649 |
| P(Bartlett's X2) | | | . | 0.675 | 0.001* | 0.056 | 0.754 |
| Mean Sep. Test | | | | SNK.05 | | SNK.05 | SNK.05 |
| Replicate F | | | 1.000 | 0.932 | 1.611 | 1.825 | 0.149 |
| Replicate Prob(F) | | | 0.4199 | 0.4494 | 0.2286 | 0.1858 | 0.9290 |
| Treatment F | | | 2.455 | 4.542 | 36.052 | 54.286 | 23.162 |
| Treatment Prob(F) | | | 0.0815 | 0.0101 | 0.0001 | 0.0001 | 0.0001 |

Means followed by same letter do not significantly differ
t=Mean descriptions are reported in transformed data units, and are not de-transformed.
Mean comparisons performed only when AOV Treatment P(F) is significant at mean comparison OSL.

Footnote 1: Pest severity (%): % of leaf area affected by the disease on 40 lettuce plants per plot

FIG. 4

| | | | | BREMLA | BREMLA | BREMLA | BREMLA | BREMLA |
|---|---|---|---|---|---|---|---|---|
| Pest Code | | | | LACSR | LACSR | LACSR | LACSR | LACSR |
| Crop Code | | | | Fresh market | Fresh market | Fresh market | Fresh market | Fresh market |
| Description | | | | LEAF C | LEAF C | LEAF C | LEAF | LEAF C |
| Part Rated | | | | 28/3/2011 | 4/4/2011 | 18/4/2011 | 3/5/2011 | 28/3/2011 |
| Rating Date | | | | PESINC | PESINC | PESINC | PESINC | CONTRO |
| Rating Type | | | | % | % | % | % | %UNCK |
| Rating Unit | | | | 40 PLANT | 40 PLANT | 40 PLANT | 40 PLANT | 40 PLANT |
| Sample Size, Unit | | | | 100 LEAF | 100 LEAF | 100 LEAF | 100 LEAF | 100 LEAF |
| Collection Basis, Unit | | | | 2 | 2 | 2 | 2 | 3 |
| Footnote Number | | | | 7 DA-A | 7 DA-B | 14 DA-C | 29 DA-C | 7 DA-A |
| Trt-Eval Interval | | | | TIO[1] | TIO[2] S05 | TIO[3] S05 | TIO[5] S05 | TAB[1] S05E |
| ARM Action Codes | | | | | | | | |
| Trt Treatment | | Rate | Appl | | | | | |
| No. Name | | Rate Unit | Code | 6 | 7 | 8 | 9 | 10 |
| 1 Untreated Check | | | | 1.9 | 10.0 a | 65.6 a | 96.3 a | 0.0 |
| 2 Bacillus subtilis strain IABBS03 | | 100 g/100 l | ABC | 0.0 | 3.1 b | 11.9 c | 58.8 b | 50.0 a |
| 3 Bacillus subtilis strain IABBS03 | | 150 g/100 l | ABC | 0.0 | 1.9 b | 10.6 c | 47.5 b | 50.0 a |
| 4 Bacillus subtilis strain IABBS03 | | 200 g/100 l | ABC | 0.0 | 1.9 b | 13.8 c | 54.4 b | 50.0 a |
| 5 CURZATE M | | 300 g/100 l | ABC | 0.0 | 1.3 b | 11.3 c | 66.3 b | 50.0 a |
| 6 SERENADE MAX | | 600 g/100 l | ABC | 0.0 | 1.3 b | 28.8 b | 55.6 b | 50.0 a |
| LSD (P=Various) | | | | 1.47 | 4.14 | 9.04 | 14.76 | 0.00 |
| Standard Deviation | | | | 0.98 | 2.75 | 6.00 | 9.80 | 0.00 |
| CV | | | | 312.69 | 85.1 | 25.38 | 15.52 | 0.0 |
| Grand Mean | | | | 0.31 | 3.23 | 23.65 | 63.13 | 50.0 |
| Bartlett's X2 | | | | 0.0 | 2.817 | 8.099 | 5.876 | 0.0 |
| P(Bartlett's X2) | | | | . | 0.728 | 0.151 | 0.318 | . |
| Mean Sep. Test | | | | | SNK.05 | SNK.05 | SNK.05 | SNK.05 |
| Replicate F | | | | 1.000 | 1.138 | 1.896 | 1.046 | 0.000 |
| Replicate Prob(F) | | | | 0.4199 | 0.3656 | 0.1736 | 0.4011 | 1.0000 |
| Treatment F | | | | 2.455 | 6.076 | 52.142 | 12.530 | 0.000 |
| Treatment Prob(F) | | | | 0.0815 | 0.0029 | 0.0001 | 0.0001 | 1.0000 |

Means followed by same letter do not significantly differ
t=Mean descriptions are reported in transformed data units, and are not de-transformed.
Mean comparisons performed only when AOV Treatment P(F) is significant at mean comparison OSL.

Footnote 2: Disease incidence (%): % of leaves affected by the disease on 40 lettuce plants
Footnote 3: Abbot (%) efficacy according to disease severity

FIG. 5

| Pest Code | | | BREMLA | BREMLA | BREMLA | BREMLA | BREMLA |
|---|---|---|---|---|---|---|---|
| Crop Code | | | LACSR | LACSR | LACSR | LACSR | LACSR |
| Description | | | Fresh market | Fresh market | Fresh market | Fresh market | Fresh market |
| Part Rated | | | LEAF C | LEAF C | LEAF - | LEAF C | LEAF C |
| Rating Date | | | 4/4/2011 | 18/4/2011 | 3/5/2011 | 28/3/2011 | 4/4/2011 |
| Rating Type | | | CONTRO | CONTRO | CONTRO | CONTRO | CONTRO |
| Rating Unit | | | %UNCK | %UNCK | %UNCK | %UNCK | %UNCK |
| Sample Size, Unit | | | 40 PLANT | 40 PLANT | 40 PLANT | 40 PLANT | 40 PLANT |
| Collection Basis, Unit | | | 100 LEAF | 100 LEAF | 100 LEAF | 100 LEAF | 100 LEAF |
| Footnote Number | | | 3 | 3 | 3 | 4 | 4 |
| Trt-Eval Interval | | | 7 DA-B | 14 DA-C | 29 DA-C | 7 DA-A | 7 DA-B |
| ARM Action Codes | | | TAB[2] S05E | TAB[3] S05E | TAB[5] S05E | TAB[6] S05E | TAB[7] S05E |
| Trt Treatment No. Name | Rate Rate Unit | Appl Code | 11 | 12 | 13 | 14 | 15 |
| 1 Untreated Check | | | 0.0 | 0.0 | 0.0 | 0.0 | 0.0 |
| 2 Bacillus subtilis strain IABBS03 | 100 g/100 l | ABC | 50.4 a | 88.3 a | 63.0 a | 50.0 a | 68.8 a |
| 3 Bacillus subtilis strain IABBS03 | 150 g/100 l | ABC | 75.7 a | 90.5 a | 79.6 a | 50.0 a | 79.2 a |
| 4 Bacillus subtilis strain IABBS03 | 200 g/100 l | ABC | 75.0 a | 85.6 a | 67.0 a | 50.0 a | 75.0 a |
| 5 CURZATE M | 300 g/100 l | ABC | 81.7 a | 87.8 a | 72.2 a | 50.0 a | 83.3 a |
| 6 SERENADE MAX | 600 g/100 l | ABC | 87.5 a | 67.4 b | 72.5 a | 50.0 a | 91.7 a |
| LSD (P=Various) | | | 46.52 | 14.49 | 15.83 | 0.00 | 41.74 |
| Standard Deviation | | | 30.19 | 9.40 | 10.27 | 0.00 | 27.09 |
| CV | | | 39.7 | 11.2 | 14.49 | 0.0 | 34.04 |
| Grand Mean | | | 76.05 | 83.93 | 70.87 | 50.0 | 79.58 |
| Bartlett's X2 | | | 2.483 | 14.51 | 1.146 | 0.0 | 4.372 |
| P(Bartlett's X2) | | | 0.648 | 0.006* | 0.887 | | 0.358 |
| Mean Sep. Test | | | SNK.05 | SNK.05 | SNK.05 | SNK.05 | SNK.05 |
| Replicate F | | | 2.098 | 0.275 | 3.475 | 0.000 | 2.175 |
| Replicate Prob(F) | | | 0.1540 | 0.8422 | 0.0506 | 1.0000 | 0.1439 |
| Treatment F | | | 0.450 | 3.978 | 1.482 | 0.000 | 0.407 |
| Treatment Prob(F) | | | 0.7708 | 0.0279 | 0.2684 | 1.0000 | 0.8002 |

Means followed by same letter do not significantly differ
t=Mean descriptions are reported in transformed data units, and are not de-transformed.
Mean comparisons performed only when AOV Treatment P(F) is significant at mean comparison OSL.

Footnote 3: Abbot (%) efficacy according to disease severity
Footnote 4: Abbot (%) efficacy according to disease incidence

FIG. 6

| Pest Code | BREMLA | BREMLA |
|---|---|---|
| Crop Code | LACSR | LACSR |
| Description | Fresh market | Fresh market |
| Part Rated | LEAF C | LEAF - |
| Rating Date | 18/4/2011 | 3/5/2011 |
| Rating Type | CONTRO | CONTRO |
| Rating Unit | %UNCK | %UNCK |
| Sample Size, Unit | 40 PLANT | 40 PLANT |
| Collection Basis, Unit | 100 LEAF | 100 LEAF |
| Footnote Number | 4 | 4 |
| Trt-Eval Interval | 14 DA-C | 29 DA-C |
| ARM Action Codes | TAB[8] S05E | TAB[9] S05E |

| Trt No. | Treatment Name | Rate | Rate Unit | Appl Code | 16 | 17 |
|---|---|---|---|---|---|---|
| 1 | Untreated Check | | | | 0.0 | 0.0 |
| 2 | Bacillus subtilis strain IABBS03 | 100 | g/100 l | ABC | 81.8 a | 38.7 a |
| 3 | Bacillus subtilis strain IABBS03 | 150 | g/100 l | ABC | 83.9 a | 50.4 a |
| 4 | Bacillus subtilis strain IABBS03 | 200 | g/100 l | ABC | 79.0 a | 43.1 a |
| 5 | CURZATE M | 300 | g/100 l | ABC | 82.8 a | 30.9 a |
| 6 | SERENADE MAX | 600 | g/100 l | ABC | 56.4 b | 42.1 a |
| LSD (P=Various) | | | | | 15.18 | 16.05 |
| Standard Deviation | | | | | 9.85 | 10.42 |
| CV | | | | | 12.83 | 25.37 |
| Grand Mean | | | | | 76.79 | 41.06 |
| Bartlett's X2 | | | | | 7.188 | 1.947 |
| P(Bartlett's X2) | | | | | 0.126 | 0.745 |
| Mean Sep. Test | | | | | SNK.05 | SNK.05 |
| Replicate F | | | | | 1.379 | 2.967 |
| Replicate Prob(F) | | | | | 0.2964 | 0.0747 |
| Treatment F | | | | | 5.484 | 1.867 |
| Treatment Prob(F) | | | | | 0.0095 | 0.1810 |

Means followed by same letter do not significantly differ
t=Mean descriptions are reported in transformed data units, and are not de-transformed.
Mean comparisons performed only when AOV Treatment P(F) is significant at mean comparison OSL.

Footnote 4: Abbot (%) efficacy according to disease incidence

FIG. 7A

Pest Code
BREMLA, Bremia lactucae, = US
Crop Code
LACSR, BVNH, Lactuca sativa var. romana, = US
Part Rated
LEAF = foliage
C = Crop is Part Rated
Rating Type
PESSEV = pest severity
PESINC = pest incidence
CONTRO = control / burndown or knockdown
Rating Unit
%AREA = percent of area
% = percent
%UNCK = percent of untreated check PLANT = plant/plant biomass/shrub LEAF = leaf
ARM Action Codes
S05 = Perform 5% Student-Newman-Keuls mean separation on Standardized Summary
TL[3] = LOG([3]+ 1)
TIO[1] = % Incidence (&0 = none)[1]
TIO[2] = % Incidence (&0 = none)[2]
TIO[3] = % Incidence (&0 = none)[3]
TIO[5] = % Incidence (&0 = none)[5]
TAB[1] = Abbott (% of Untreated)[1]
TAB[2] = Abbott (% of Untreated)[2]
TAB[3] = Abbott (% of Untreated)[3]
TAB[5] = Abbott (% of Untreated)[5]
TAB[6] = Abbott (% of Untreated)[6]
TAB[7] = Abbott (% of Untreated)[7]
TAB[8] = Abbott (% of Untreated)[8]
TAB[9] = Abbott (% of Untreated)[9]

Footnote 1: Pest severity (%): % of leaf area affected by the disease on 40 lettuce plants per plot
Footnote 2: Disease incidence (%): % of leaves affected by the disease on 40 lettuce plants
Footnote 3: Abbot (%) efficacy according to disease severity
Footnote 4: Abbot (%) efficacy according to disease incidence

FIG. 7B

| | Trial Location | | |
|---|---|---|---|
| City: | Bullas | Latitude of LL Corner °: | 37.959194 N |
| State/Prov.: | Murcia | Longitude of LL Corner °: | 1.649181 W |
| Postal Code: | 30180 | Altitude of LL Corner, Unit: | 693.00 m |
| Country: | ESP Spain | | |
| Map Reference: | Google Earth (WGS84) | Angle y-axis to North °: | 45.00 |
| Directions: | | | |

- Poligono 152, Parcela 9, Recinto 7 (SIGPAC).
- Farm name: Francés.

Official Trial Code: AS 02611 F 01
Conducted Under GEP: Yes    Other Trial Code: AS 02611 F 01

| | Guideline | Description |
|---|---|---|
| 1. | PP 1/152(3) | Design and analysis of efficacy evaluation trials |
| 2. | PP 1/181(3) | Conduct and reporting of efficacy evaluation trials including GEP |
| 3. | PP 1/38(3) | Monilinia laxa |
| 4. | PP 1/135(3) | Phytotoxicity assessment |

Objectives:

- Efficacy and selectivity of EXPERIMENTAL P. against *Monilinia laxa* in apricot trees.
- Appropriate rate of EXPERIMENTAL P..
- Comparison with the reference Folicur 25 WG.

| | Crop Description | | |
|---|---|---|---|
| Crop 1: | PRNAR  Prunus armeniaca | Apricot | |
| Variety: | Bulida | | |
| BBCH Scale: | BSTO | Planting Date: | 1/4/1993 |
| Planting Method: | TRAHAN  transplanted - hand | Rate, Unit: | 204 P/HA |
| | | Perennial Age, Unit: | 18 YR |
| Row Spacing, Unit: 7.0 m | | Spacing Within Row, Unit: | 7.0 m |

| | Pest Description |
|---|---|
| Pest 1 Type: D  Code: MONILA  Monilinia laxa | |
| Common Name: | Blossom blight |

| | | Site and Design | |
|---|---|---|---|
| Plot Width, Unit: | 7 m | Site Type: | ORCHAR  orchard |
| Plot Length, Unit: | 14 m | Experimental Unit: 1 | PLOT  plot |
| Plot Area, Unit: | 98 m2 | Tillage Type: | CONTIL  conventional-till |
| Replications: | 4 | Study Design: | RACOBL  Randomized Complete Block (RCB) |
| | | Untreated Arrangement: | INCLUDED  single control randomized in each block |

Trial Initiation Comments:

- Drip irrigation according to trees necessities.
- Crop in commercial production.
- Plot size including 2 trees.
- Crop stage at the first application timing BBCH: 59-60 (Most flowers with petals forming a hollow ball - First flowers open).
- Trees in free form.

Comment: No agrochemical product was applied in the whole trial area against any pest.

FIG. 8A

Soil Description

% Sand: 35.0  % OM: 1.03  Texture: CL clay loam
% Silt: 28.0  pH: 8.2
% Clay: 37.0  Fert. Level: G good
Soil Drainage: G good

Additional Measured Elements

| Element | Quantity | Unit |
|---|---|---|
| Organic carbon | 0.60 | % |
| Total organic matter | 1.34 | % |

Moisture and Weather Conditions

Overall Moisture Conditions: ABONOR above normal
Closest Weather Station: Mula (ML21)  Distance, Unit: 18,39 km

| No. | Date | Amount | Unit | Type | Type Description | Min Temp | Max Temp | Temp Unit | Relative Humidity |
|---|---|---|---|---|---|---|---|---|---|
| 1. | 15/2/2011 | 2,7 | mm | RAIN | rain | 6,6 | 12,1 | C | 80,2 |
| 2. | 16/2/2011 | 0,0 | mm | RAIN | rain | 6,6 | 17,1 | C | 57,8 |
| 3. | 17/2/2011 | 2,0 | mm | RAIN | rain | 5,1 | 16,2 | C | 52,9 |
| 4. | 18/2/2011 | 0,1 | mm | RAIN | rain | 9,3 | 20,1 | C | 51,7 |
| 5. | 19/2/2011 | 0,0 | mm | RAIN | rain | 7,5 | 20,4 | C | 56,2 |
| 6. | 20/2/2011 | 0,5 | mm | RAIN | rain | 10,5 | 20,3 | C | 59,6 |
| 7. | 21/2/2011 | 0,0 | mm | RAIN | rain | 14,1 | 20,5 | C | 44,6 |
| 8. | 22/2/2011 | 0,0 | mm | RAIN | rain | 12,1 | 22,3 | C | 49,8 |
| 9. | 23/2/2011 | 0,0 | mm | RAIN | rain | 9,2 | 23,9 | C | 51,7 |
| 10. | 24/2/2011 | 0,0 | mm | RAIN | rain | 8,6 | 23,6 | C | 62,4 |
| 11. | 25/2/2011 | 0,0 | mm | RAIN | rain | 6,6 | 21,0 | C | 65,2 |
| 12. | 26/2/2011 | 0,0 | mm | RAIN | rain | 9,0 | 28,8 | C | 40,7 |
| 13. | 27/2/2011 | 0,0 | mm | RAIN | rain | 8,7 | 18,3 | C | 47,7 |
| 14. | 28/2/2011 | 0,3 | mm | RAIN | rain | 6,8 | 15,7 | C | 40,7 |
| 15. | 1/3/2011 | 0,0 | mm | RAIN | rain | 2,8 | 15,9 | C | 45,1 |
| 16. | 2/3/2011 | 0,0 | mm | RAIN | rain | 4,4 | 17,0 | C | 43,9 |
| 17. | 3/3/2011 | 4,1 | mm | RAIN | rain | 5,8 | 15,8 | C | 58,2 |
| 18. | 4/3/2011 | 1,9 | mm | RAIN | rain | 7,4 | 11,9 | C | 86,7 |
| 19. | 5/3/2011 | 0,9 | mm | RAIN | rain | 7,1 | 14,6 | C | 81,2 |
| 20. | 6/3/2011 | 0,0 | mm | RAIN | rain | 6,7 | 16,9 | C | 76,3 |
| 21. | 7/3/2011 | 0,0 | mm | RAIN | rain | 6,8 | 18,1 | C | 72,5 |
| 22. | 8/3/2011 | 0,0 | mm | RAIN | rain | 7,9 | 14,9 | C | 79,6 |
| 23. | 9/3/2011 | 0,0 | mm | RAIN | rain | 10,7 | 13,5 | C | 78,2 |
| 24. | 10/3/2011 | 0,4 | mm | RAIN | rain | 9,6 | 13,4 | C | 81,1 |
| 25. | 11/3/2011 | 30,1 | mm | RAIN | rain | 9,7 | 12,3 | C | 95,2 |
| 26. | 12/3/2011 | 9,1 | mm | RAIN | rain | 9,5 | 18,5 | C | 85,3 |
| 27. | 13/3/2011 | 0,0 | mm | RAIN | rain | 9,5 | 21,2 | C | 71,2 |
| 28. | 14/3/2011 | 4,6 | mm | RAIN | rain | 11,4 | 19,2 | C | 85,8 |
| 29. | 15/3/2011 | 0,6 | mm | RAIN | rain | 11,1 | 19,0 | C | 67,7 |
| 30. | 16/3/2011 | 0,0 | mm | RAIN | rain | 10,3 | 20,0 | C | 44,0 |
| 31. | 17/3/2011 | 0,0 | mm | RAIN | rain | 14,8 | 21,9 | C | 45,4 |
| 32. | 18/3/2011 | 0,0 | mm | RAIN | rain | 11,4 | 24,4 | C | 49,3 |
| 33. | 19/3/2011 | 0,0 | mm | RAIN | rain | 9,4 | 26,5 | C | 52,7 |
| 34. | 20/3/2011 | 0,0 | mm | RAIN | rain | 7,5 | 20,6 | C | 67,2 |
| 35. | 21/3/2011 | 0,0 | mm | RAIN | rain | 10,6 | 16,9 | C | 76,6 |
| 36. | 22/3/2011 | 0,2 | mm | RAIN | rain | 10,1 | 16,0 | C | 65,3 |

FIG. 8B

| | Application Description | | |
|---|---|---|---|
| | A | B | C |
| Application Date: | 2/3/2011 | 7/3/2011 | 14/3/2011 |
| Time of Day: | 15.00 | 9.00 | 8.00 |
| Application Method: | SPRAY | SPRAY | SPRAY |
| Application Timing: | ATBLST | ATBLOO | ATBLOO |
| Application Placement: | FOLIAR | FOLIAR | FOLIAR |
| Applied By: | JSA | JSA | JSA |
| Air Temperature, Unit: | 13.6 C | 12.2 C | 10.8 C |
| % Relative Humidity: | 41 | 76 | 90 |
| Wind Velocity, Unit: | 1 MPS | 0.5 MPS | 0 MPS |
| Wind Direction: | N | N | |
| Dew Presence (Y/N): | N no | N no | N no |
| Soil Temperature, Unit: | 9.9 C | 7.4 C | 8.6 C |
| Soil Moisture: | DRY | DRY | SLWET |
| % Cloud Cover: | 10 | 5 | 100 |
| Next Rain Occurred On: | 3/3/2011 | 10/3/2011 | 15/3/2011 |

| | Crop Stage At Each Application | | |
|---|---|---|---|
| | A | B | C |
| Crop 1 Code, BBCH Scale: | PRNAR BSTO | PRNAR BSTO | PRNAR BSTO |
| Stage Scale Used: | BBCH | BBCH | BBCH |
| Stage Majority, Percent: | 59  90 | 59  75 | 65  100 |
| Stage Minimum, Percent: | 59  90 | 59  75 | 65  100 |
| Stage Maximum, Percent: | 60  10 | 61  25 | 65  100 |
| Diameter, Unit: | 4.5  m | 4.5  m | 4.5  m |
| Height, Unit: | 3.00  m | 3.00  m | 3.00  m |
| Height Minimum, Maximum: | 2.90  3.25 | 2.90  3.25 | 2.90  3.25 |
| Plant Foliage Height, Unit: | 2.00  m | 2.00  m | 2.00  m |
| Crop coverage (%): | 30 | 30 | 30 |

| | Pest Stage At Each Application | | |
|---|---|---|---|
| | A | B | C |
| Pest 1 Code, Type, Scale: | MONILA D | MONILA D | MONILA D |
| Stage Majority, Percent: | PRINFC 100 | PRINFC 100 | PRINFC 100 |

| | Application Equipment | | |
|---|---|---|---|
| | A | B | C |
| Appl. Equipment: | MARUYAMA | MARUYAMA | MARUYAMA |
| Equipment Type: | BACSPR | BACSPR | BACSPR |
| Operating Pressure, Unit: | 1200  kPa | 1200  kPa | 1200  kPa |
| Nozzle Type: | Sol. cone | Sol. cone | Sol. cone |
| Nozzle Size: | MARTI 1.5 | MARTI 1.5 | MARTI 1.5 |
| Nozzles/Row: | 1 | 1 | 1 |
| Nozzle Calibration, Unit: | 3870  ML/MIN | 3870  ML/MIN | 3870  ML/MIN |
| Ground Speed, Unit: | 1.0  KPH | 1.0  KPH | 1.0  KPH |
| Carrier: | WATER | WATER | WATER |
| Spray Volume, Unit: | 1002.2 L/ha | 1000.6 L/ha | 1000.1 L/ha |
| Mix Size, Unit: | 44  liters | 44  liters | 44  liters |
| Spray pH: | 7.5 | 7.5 | 7.5 |
| Propellant: | PUMP | PUMP | PUMP |
| Tank Mix (Y/N): | N no | N no | N no |

Equipment Comment: "Maruyama" is a backpack sprayer with a motor-pump appropriate to use in small plots simulating the common practice.

| Trt No | Treatment Application Comment |
|---|---|
| 2, 3 and 4 | No problem was observed neither during the handling of products, nor in the dissolution in water or later on in the application equipment independently of the used rate. |
| 5 | Reference product. Applications without problems. |

| Date | By | Notes |
|---|---|---|
| 2/3/2011 | JSA | Previously to the spray, the needed verifications were carried out to determine the appropriate volume rate according to the protocol. |
| 2/3/2011 | JSA | Application (A). The equipment was cleaned with an organic solvent (ammonia) between treatments with different formulation, active ingredient, etc. |
| 7/3/2011 | JSA | Application (B). |
| 14/3/2011 | JSA | Application (C). |
| 22/3/2011 | JSA | Assessment on at least 50 shoots per plot. number of healthy shoots, shoots with affected flowers, healthy flowers and affected flowers. |

FIG. 9A

Additional Information (Validation List Comments)

F, fungicide = fungicide|
F, one-year/final = one-year/final|6
N, N = North
W, W = West
ESP, 43.772217, 27.637497, -18.170559, 4.316944 = Spain
m = meters
PP 1/152(3), Design and analysis of efficacy evaluation trials = EPPO|
PP 1/181(3), Conduct and reporting of efficacy evaluation trials including GEP = EPPO|
PP 1/38(3), Monilinia laxa = EPPO|
PP 1/135(3), Phytotoxicity assessment = EPPO|
PRNAR, BSTO, Prunus armeniaca, = US
TRAHAN, transplanted - hand = transplanted - hand
P/HA = plant per hectare
YR = year
m = meter
D, Disease, G-BYRD7, G-DisStg = Disease, such as a fungus, bacteria, or virus
MONILA, Monilinia laxa, = US
ORCHAR, orchard = orchard
PLOT, plot = plot
CONTIL, conventional-till = conventional-till
RACOBL, Randomized Complete Block (RCB) = Randomized Complete Block (RCB)
INCLUDED, single control randomized in each block = single control randomized in each block
CL, clay loam = clay loam
G, good = good
G, good = Good / medium / adequate drainage with aeration not likely to harm crop growth
ABONOR, above normal = above normal
km = kilometer
mm = millimeter
RAIN, rain = rain
C = Celsius
SPRAY = spray
ATBLST = at flowering start
FOLIAR = foliar
JSA = Joaquín Soler Álvarez
MPS = meter per second
N = North
N, no = no
DRY = dry
ATBLOO = at blossom (bloom)
SLIWET = slightly wet
BBCH = BBCH uniform plant stages
59 = Most flowers with petals forming a hollow ball|BSTO
60 = First flowers open|BSTO
61 = Beginning of flowering: about 10% of flowers open|BSTO
65 = Full flowering: at least 50% of flowers open, first petals falling|BSTO
PRINFC = Pre-Infection
BACSPR = backpack sprayer, knapsack sprayer, hand held sprayer
kPa = kilopascal
ML/MIN = Milliliter per minute
KPH = kilometer per hour
WATER = water
L/ha = liters per hectare
liters = liters of mix
PUMP = pump

FIG. 9B

| Trt No. | Type | Treatment Name | Form Conc | Form Unit | Form Type | Lot Code | Description | Rate | Rate Unit | Appl Code |
|---|---|---|---|---|---|---|---|---|---|---|
| 1 | CHK | Untreated Check | | | | | not treated | | | |
| 2 | FUNG | EXPERIMENTAL P. | $10^9$ | CFU/g | WP | BS81101011 | Bacillus subtilis strain IAB/BS/03 | 0,2 | kg/100 l | ABC |
| 3 | FUNG | EXPERIMENTAL P. | $10^9$ | CFU/g | WP | BS81101011 | Bacillus subtilis strain IAB/BS/03 | 0,5 | kg/100 l | ABC |
| 4 | FUNG | EXPERIMENTAL P. | $10^9$ | CFU/g | WP | BS81101011 | Bacillus subtilis strain IAB/BS/03 | 1,0 | kg/100 l | ABC |
| 5 | FUNG | Folicur 25 WG | 25 | % | WG | EQ13000608 | Tebuconazole | 0,075 | kg/100 l | ABC |

Replications: 4, Untreated treatments: 1, Conduct under GLP/GEP: Yes (GEP with no protection), Design: Randomized Complete Block (RCB), Treatment units: Treated 'Plot' size, Dry Form. Unit: %, Treated 'Plot' size Width: 7 meters, Treated 'Plot' size Length: 14 meters, Application volume: 1002.2 L/ha, Mix size: 44 liters, Mix overage: 4720 ml, Format definitions: G-All7.def, G-All7.frm

FIG. 10

*Monilinia laxa* in apricot trees: percentage of shoots with affected flowers and percentage of affected flowers in at least 50 shoots per plot

SHOOTS

| Treatment | % Shoots with affected flowers (ANOVA) 22.03.11 (8 DA-C) | % Efficacy (Abbott formula) 22.03.11 (8 DA-C) |
|---|---|---|
| 1.- UNTREATED CHECK | 40.91 a | - |
| 2.- EXPERIMENTAL PRODUCT (200 g/hl) | 7.00 c | 81.7 |
| 3.- EXPERIMENTAL PRODUCT (500 g/hl) | 21.51 b | 46.8 |
| 4.- EXPERIMENTAL PRODUCT (1000 g/hl) | 15.50 b | 59.9 |
| 5.- FOLICUR 25 WG (75 g/hl) | 5.00 c | 88.5 |

FLOWERS

| Treatment | % Affected flowers (ANOVA) 22.03.11 (8 DA-C) | % Efficacy (Abbott formula) 22.03.11 (8 DA-C) |
|---|---|---|
| 1.- UNTREATED CHECK | 8.38 a | - |
| 2.- EXPERIMENTAL PRODUCT (200 g/hl) | 1.37 b | 82.8 |
| 3.- EXPERIMENTAL PRODUCT (500 g/hl) | 2.10 b | 74.8 |
| 4.- EXPERIMENTAL PRODUCT (1000 g/hl) | 1.41 b | 82.9 |
| 5.- FOLICUR 25 WG (75 g/hl) | 0.42 c | 95.2 |

DA-C: days after application C

FIG. 11A

SHOOTS

| Treatment | % Shoots with affected flowers (ANOVA) 22.03.11 (8 DA-C) | % Efficacy (Abbott formula) 22.03.11 (8 DA-C) |
|---|---|---|
| 1.- UNTREATED CHECK | 96.00 a | - |
| 2.- EXPERIMENTAL PRODUCT (200 g/hl) | 45.00 b | 53.7 |
| 3.- EXPERIMENTAL PRODUCT (500 g/hl) | 60.00 b | 38.2 |
| 4.- EXPERIMENTAL PRODUCT (1000 g/hl) | 47.00 b | 51.7 |
| 5.- FOLICUR 25 WG (75 g/hl) | 8.50 c | 91.1 |

FLOWERS

| Treatment | % Affected flowers (ANOVA) 22.03.11 (8 DA-C) | % Efficacy (Abbott formula) 22.03.11 (8 DA-C) |
|---|---|---|
| 1.- UNTREATED CHECK | 74.27 a | - |
| 2.- EXPERIMENTAL PRODUCT (200 g/hl) | 12.74 b | 84.0 |
| 3.- EXPERIMENTAL PRODUCT (500 g/hl) | 26.94 b | 65.2 |
| 4.- EXPERIMENTAL PRODUCT (1000 g/hl) | 30.26 b | 62.6 |
| 5.- FOLICUR 25 WG (75 g/hl) | 0.92 c | 98.6 |

DA-C: days after application C

FIG. 11B

STRAIN OF *BACILLUS SUBTILIS* FOR COMBATING PLANT DISEASES

This application is the National Stage of International Application No. PCT/ES2012/070310, filed May 4, 2012, and claims priority to Spanish Application No. P201131743, filed Oct. 28, 2011.

The present invention falls within the field of biopesticides. More concretely, this invention relates to the discovery of a new *Bacillus subtilis* strain, (IAB/BS03), which can inhibit a wide range of fungal and bacterial diseases of plants. The invention also relates to fungicidal compositions comprising said new strain of *Bacillus subtilis*, either alone, as part of a formulation, or in combination with other chemical and biological pesticides.

STATE OF THE ART

Several microorganisms are known for exhibiting biological activity and are useful in plant disease control. Although progress has been made in the field of identification and development of biological pesticides for controlling several plant diseases of agricultural importance, such as fruit trees and diverse horticultural products, most of the pesticides in use are still synthetic compounds. Most of these chemical fungicides are classified as carcinogenic in our current European regulation, and also in EPA, and they have been shown to be toxic for wildlife and other species that are not their target. Furthermore, these synthetic chemical compounds induce a resistance phenomenon in lots of cases, whereby pathogen(s) repeatedly treated with these compounds end up being immune and resistant to the treatment, so that control over the pest or disease would become ineffective (Schwinn et al., p. 244, *Advances in plant pathology: Phytophthora infestans*, the cause of late blight of potato (Academic press, San Diego, 1991)).

The biological activity of different microorganism types against plant pests and diseases has been described. Specifically, strains of *Bacillus* spp (*Bacillus* spp. includes *B. subtilis, B. cereus, B. thuringiensis*, among others) have been described to exhibit activity against various field pests (Stabb et al. (1990), Applied Environ. Microbiol. 60: 4404-4412). This activity may be due to different mechanisms of action, among which are the production of antibiotics that inhibit the development of fungi and bacteria, or the production of toxins which act specifically and selectively against certain types of insects.

In U.S. Pat. Nos. 4,999,192 and 5,208,017 it is described that pesticide strains of *B. thuringiensis* produce crystalline proteins during sporulation, which are specifically toxic to certain orders and species of insects and nematodes.

In general, *Bacillus subtilis* and its closely related species are considered non pathogenic microorganisms, accepted as GRAS (Generally Regarded As Safe), by the US Food and Drug Administration (US EPA). Nonetheless, it is difficult to characterize a *Bacillus subtilis* species so as to differentiate it from other species such as *Bacillus cereus* or *Bacillus thuringiensis*. *Bacillus cereus* is species closely related species to *Bacillus subtilis*, but nevertheless causes gastroenteritis and opportunistic infections when found as a contaminant in the food chain. *Bacillus thuringiensis* is a microorganism widely used as a bioinsecticide; however, its action spectrum in terms of pests (insects) is very different from *Bacillus subtilis*, whose action spectrum is, preferably, phytopathogenic fungi.

There are numerous patent documents based on *Bacillus Cereus* strains. U.S. Pat. No. 5,049,379 by Handelsman et al. describes the coating of seeds with a specific *Bacillus cereus* strain (ATCC 53522), that inhibits the pathogenic activity of the root rot fungi. It also describes how application of formulations based on spores of certain *Bacillus cereus* strains applied to soya seeds or to the soil surrounding the seeds improves soya yields (Osburne et al. (1995), Am. Phytopathol. Soc. 79(6); Smith et al (1993)).

In the state of the art, it has also been described that the activity of the soil pathogenic fungus, *Pythium aphanidermatum*, in cucumber cultivation may be suppressed by using the UW strain of *B. cereus* (Plant Disease 77(2), 139-142).

The action spectrum of different *Bacillus* is determined not only by the species, but also by the specific strain being studied. Furthermore, using species such as *Bacillus cereus* or *Bacillus thuringiensis* as biocontrol agents would not be adequate as it is a food contaminant, whose presence in the food chain is prohibited.

With regard to *Bacillus subtilis* and other closely related species (*B. pumilus, B. polymyxa, B. megatherium*, etc.), there also exist numerous bibliographic references and patent documents referring to their antifungal effect by means of antibiotic production (Leifert et al. (1995), J. Appl. Bacteriol. 78: 97-108, Astilbe; Leifert et al. (1997) U.S. Pat. No. 5,597,565; Rossall (1994), U.S. Pat. No. 5,344,647, Sholberg et al. (1995), Can. J. Microbiol. 41: 247-252; Swinburne et al. (1975), Trans. Brit. Mycol. Soc. 65: 211-217; Singh and Deverall (1984), Trans. Br. Mycol. Soc. 83: 487-490, and Ferreira et al. (1991), Phytopathology 81: 283-287).

The use of *Bacillus* spp. and *Bacillus subtilis* as biocontrol agents for fungal plant pathogens has been described (Baker et al. (1983), Phytopathology 73: 1148-1152, Pusey et al. (1988), Plant Dis. 72: 622-626; Pusey and Robins (U.S. Pat. No. 5,047,239) and McKeen et al. (1986), Phytopathology 76: 136-139).

That is to say that the fungicidal activity, by means of antibiotic production from different strains of *Bacillus subtilis* and other closely related species is well documented. Even registers of this antibiotic production, in particular of the *B. megaterium*, are found by Berdy in the CRC Handbook of Antibiotic Compounds, Vol. I-XIV (CRC Press, Inc., Boca Ratón, Fla., 1980-87).

However, there are no commercially available products based on any of the antibiotics produced by the different strains of *Bacillus*. A group of researchers, based on their work with a series *Bacillus* strains that produce iturins (antibiotic produced by *Bacillus* strains), claim that the amounts of iturins obtained by natural production are inadequate in order to be commercially feasible (Bland et al. (1995), Proc. Plant Growth Regulation Soc. Am. $22^{nd}$: 105-107)). For this reason, applications on field are made with solid or liquid formulations containing spores of bacilli, which exert their action once their development begins in the ecological niche offered to them, provided that they have the necessary requirements to reproduce.

Patent documents ES2268774 and EP0981540B1 describe the AQ713 strain of *Bacillus subtilis*, identical to QST 713 strain, as a strain producer of antibiotics and metabolites which exhibits a wide fungicidal and bactericidal activity. This patent document describes the use of said strain in a method for the treatment or protection of plants, and against fungal and bacterial infections. Said strain is currently marketed as a moisturizable or wettable powder, i.e., what is marketed is the resistance form of said strain, the *Bacillus subtilis* QST 713 spore. Nevertheless, the QST 713 strain of *Bacillus subtilis* shows no fungicidal activity or it is not powerful enough against the fungal disease lettuce mildew (*Bremia lactucae*), so its application in plant treatment or protection is not completely efficient. In example 4 of the present invention, a commercial product containing QST 713 strain of *Bacillus subtilis* is used, and its efficiency as fungicidal agent is compared to that of the *Bacillus subtilis* strain object of the present invention against the fungal disease lettuce mildew (*Bremia lactucae*). In example 8, paragraph 55 of Patents ES2268774 and EP0981540B1, it is observed that the QST 713 strain did not prevent the downy mildew (lettuce mildew or *Bremia*), whereas the *Bacillus subtilis* strain object of the present invention indeed presents activity against said disease. Additionally, it is worth mentioning that the *Bacillus subtilis* strain object of the present invention presents the same efficiency levels as a commercial chemical fungicide, mancozeb+cymoxanil 4% (CURZATE M), using a 300 times smaller dose than the applied dose of QST 713 strain of *Bacillus subtilis*.

Therefore, there is currently a need to identify a *Bacillus subtilis* strain different from QST 713 strain of *Bacillus subtilis*, with different bactericide and fungicide activity, for use as a biopesticide in the protection and/or treatment of plants against pathogenic infections, preferably against phytopathogenic fungi infections, and more preferably against lettuce mildew.

BRIEF DESCRIPTION OF THE INVENTION

The present invention relates to a *Bacillus subtilis* strain different from other specific *Bacillus subtilis* strains which are currently commercially available (e.g. QST 713 strain of *Bacillus subtilis*), and which presents bactericidal and/or fungicidal activity, characterized in that the antibiotics that it produces have a great potency and, in addition, its combination produces different specificities against plant diseases. Said *Bacillus subtilis* strain is used in a method for the treatment or protection of plants against fungal and/or bacterial infections that consists on applying an effective amount thereof, characterized in that it is smaller than the amount needed with other *Bacillus subtilis* strains currently commercially available (as for example QST 713 strain of *Bacillus subtilis*).

The *Bacillus subtilis* strain object of the present invention may be presented in any of the known forms to one skilled in the art: in spore form, as a solid, granulated or liquid formulation, as an activated culture, or even as the supernatant of the suspension of said activated culture where the produced metabolites are present, etc.

DETAILED DESCRIPTION OF THE INVENTION

*Bacillus subtilis* Strain (DSM 24682)

The following strain has been deposited on the 6 Jun. 2011, at the German Type Culture Collection (DSMZ), Inhoffenstraβe 7 B, 38124 Braunschweig (Germany) by Ms. Estefania Hinajeros Esteve, IAB, S. L. (Investigaciones y Aplicaciones Biotecnológicas, S. L.), Avda. Paret del Patriarca 11-B, Ap.30, 46113 Moncada, Valencia (Spain).

The deposit of the deposited strain whose reference is *Bacillus subtilis* var. subtilis designated as IAB/BS03, CECT 7254, was identified by the DSMZ with the accession number DSM 24682 once said International Depositary Authority declared that said strain in question was viable, under the stipulations of the Budapest Treaty on the International Recognition of the Deposit of Microorganisms for the Purpose of Patent Procedure.

The DSM 24682 strain of *Bacillus subtilis* presents a wide antifungal activity, more potent than other *Bacillus subtilis* strains, against specific diseases. The DSM 24682 strain is identified as a *Bacillus subtilis* strain differentiable from other strains, not just of *Bacillus* spp. (*B. cereus* and *B. thuringiensis*), but also from other *Bacillus subtilis* widely characterized and documented, such as QST 713 strain of *Bacillus subtilis*. Both strains produce antibiotic substances against phytopathogenic fungi, but the DSM 24682 strain is more potent in terms of specificity and selectivity in treatments, and in terms of its efficiency. The present invention allows complete control on the pathogen attack with only a small amount of said microorganism. This shows that with the same number of applications of said strain, and with a work concentration smaller than the one currently available on the market as a phytosanitary product, it presents the same efficiency as a synthetic chemical product for that particular use and compared to another strain of the same species.

The present invention has as subject matter being protected an isolated *Bacillus subtilis* IAB/BS03 strain deposited at the German Type Culture Collection DSMZ with the accession number DSM 24682, or a mutant of said strain, and also deposited at the Spanish Type Culture Collection with accession number CECT 7254, owned by the company submitting the present invention, wherein said strain and/or its mutant present antifungal and/or antibacterial activity.

Preferably, said strain presents an action profile different from other *Bacillus subtilis* strains and at least 300 times more potent in terms of its capacity to act as a biological control agent in the field.

In a preferred embodiment of the present invention, the strain previously described is protected, characterized in that it is the IAB/BS03 strain of *Bacillus subtilis* deposited at the German Type Culture Collection DSMZ with accession number DSM 24682.

In another preferred embodiment of the present invention, an active culture (fermentation) in a complete broth of the previously described strain is protected.

In another preferred embodiment of the present invention, a supernatant obtained from a culture of the previously described strain, characterized in that it exhibits antifungal and antibacterial activity, is protected.

In another preferred embodiment of the present invention, a composition at least comprising:
(i) the previously described strain;
(ii) the active culture in complete broth of the strain; or
(iii) the supernatant previously described;
is protected; said composition further preferably can comprise a chemical fungicide or a chemical or biological pesticide.

In an even more preferred embodiment, said composition further includes either a chemical fungicide or a chemical or biological pesticide.

In another preferred embodiment of the present invention, a method of use for plant and fruits protection and/or treatment against fungal and/or bacterial infections, that comprises applying an effective amount of the previously described strain, active culture in complete broth, supernatant or composition, is protected.

Preferably, said method is characterized in that it is administered at least a dose 300 times lower than the effective amount of the previously described strain, active culture in complete broth, supernatant or composition in order to achieve the same fungicidal potency compared to the administration of a different *Bacillus subtilis* strain. The DSM 24682 strain (IAB/BS03) object of the present invention is at least 300 times more potent than the QST 713 strain of *Bacillus subtilis*, as a representative example of a different specific strain of the same species (of *Bacillus subtilis*). Furthermore, the DSM 24682 strain (IAB/BS03) object of the present invention has fungicidal properties comparable to the treatment with mancozeb+cymoxanil 4% (CURZATE M), as representative example of commercially available chemical fungicide treatment.

In an even more preferred embodiment, said method is characterized in that the fungal and/or bacterial infections are caused by at least one microorganism selected from the following group: *Alternaria* sp, *Botrytis* sp, *Fusarium* sp, *Phytophthora* sp, *Rhizoctonia* sp, *Sclerotinia* sp, *Verticillium* sp, *Leveillula* sp, *Venturia* sp, *Plasmopara* sp, *Uncinula* sp, *Pythium* sp, *Colletotrichum* sp, *Cladosporium* sp, *Monilinia* sp, *Acidovorax* sp, *Pseudomonas* sp, *Xanthomonas* sp, *Erwinia* sp, *Clavibacter* sp, *Sphaerotheca* sp and *Peronospora* sp.

Preferably, said method is characterized in that the infections are caused by at least one microorganism selected from the following group: *Alternaria* sp, *Botrytis* sp, *Fusarium* sp, *Phytophthora* sp, *Rhizoctonia* sp, *Sclerotinia* sp and *Verticillium* sp.

More preferably, said method is characterized in that the infections are caused by at least one microorganism selected from the following group: *Alternaria solani, Alternaria brassiciola, Botrytis cinerea, Fusarium oxysporum, Phytophthora infestans, Rhizoctonia solani, Sclerotinia sclerotorium, Vericiffium lecanii, Leveillula taurica, Venturia inaequalis, Venturia pyrina, Plasmopara viticola, Uncinula necator, Pythium ultimurn, Colletotrichum cocodes, Cladosporium cucumerinurn, Monilinia fructicola, Acidovorax avenae, Pseudomonas syringae, Xanthomonas campestris, Erwinia carotovora, Clavibacter michiganense, Sphaerotheca fuliginea* and *Peronospora parasitica*.

Even more preferably, said method is characterized in that the infections are caused by at least one microorganism selected from the following group: *Alternaria solani, Alternaria brassiciola, Botrytis cinerea, Fusarium oxysporum, Phytophthora infestans, Rhizoctonia solani, Sclerotinia sclerotorum* and *Verticillium lecanii*.

In an even more preferred embodiment, said method is characterized in that the strain is applied as wettable powder, granules, fluids or microencapsulations.

In an even more preferred embodiment, said method is characterized in that the previously described strain, active culture in complete broth, supernatant or composition, is applied at a place chosen from the following group: roots, leaves (vegetative part), flowers, fruits and soil surrounding the roots.

In another preferred embodiment of the present invention, a composition comprising any of the antibiotics and secondary metabolites produced by the previously described strain, or combinations thereof, is protected.

The invention also includes prevention and treatment methods against fungal and bacterial infections in plants by using said bacterial strains or supernatants containing antibiotics or pure antibiotics obtained from said bacterial strains, wherein said antibiotics are contained within a composition as defined in the claims.

Given that the effects against fungal and bacterial diseases are different from those described for strain QST 713 of *Bacillus subtilis*, it will be readily understood that the combination of metabolites produced and/or antibiotics produced by the strain in question are quantitatively and qualitatively different (differentiable strain and different clearly measurable effects).

As used herein, "biological control" is defined as control of a pathogen by using a second organism. The known biological control mechanisms include bacteria and fungi capable of controlling diseases of both root and the leaf portion of the plants. From these bacteria and fungi, which are used are either toxins or secondary metabolites that are produced and isolated; or the bacterial or fungal species, applied in situ, so that said toxins and metabolites are produced once the bacteria or fungi finds what is necessary for its reproduction and development.

The term "fungus" or "fungi" includes a wide range of nucleated spore-carrier organisms that are devoid of chlorophyll. Examples of fungi are yeasts, filamentous molds and mushrooms.

The term "bacteria" includes any prokaryotic organism that does not have a differentiated nucleus.

The term "fungicide or antifungal" means the capacity of a substance to increase the mortality or inhibit the growth rate of fungi.

The term "bactericide" means the capacity of a substance to increase the mortality or inhibit the growth of bacteria.

The term "antibiotic" includes any substance capable of killing or inhibiting a microorganism. Antibiotics may be produced by a microorganism or by means of a synthetic or semi-synthetic process. The term, therefore, includes a substance that inhibits or kills fungi, for example the combination of iturines, surfactines, plipastatins, and other antibiotics, produced by different strains of *Bacillus*.

The term "culture" refers to the propagation of organisms over or in different types of mediums. "Culture in complete broth" refers to a liquid culture containing both cells and medium. "Supernatant" refers to the liquid broth that remains when the cells that have grown in the broth are separated by centrifugation, filtration, sedimentation or other means well known in the art.

An "effective amount" is an amount enough to produce beneficial or desired results. An effective amount may be administered in one or more administrations. In terms of treatment and protection, an "effective amount" is the amount enough to improve, stabilize, revert, slow down or hinder the progression of the stages of the fungal or bacterial disease.

The term "positive control" means a compound known for having pesticide activity. Such "positive controls" include, without limitation, marketed chemical pesticides. The term "negative control" means a compound known for not having pesticide activity. Examples of negative controls are water or ethyl acetate.

The term "metabolite" refers to any compound, substance or by-product of a microorganism fermentation having pesticide activity. Antibiotic, as defined herein, is a specifically active metabolite against a microorganism.

Another embodiment of the present invention provides a method for the treatment or protection of plants against fungal and bacterial infections that consists in applying an effective amount of a supernatant obtained from a culture in complete broth of DSM 24682 within the present invention. The supernatant may be obtained by well known means in the art, including centrifugation, filtration, sedimentation and the like.

In order to achieve good dispersion and adhesion of compositions within the present invention, it may be advantageous to formulate the culture in complete broth, the supernatant and/or the metabolite/antibiotic with compounds that aid dispersion and adhesion. The suitable formulations are known for those skilled in the art.

The compositions of the present invention may be formulated as a wettable powder, granules and the like, or may be microencapsulated in a suitable means and the like. Examples of other formulations include, but without limitation, soluble powder, wettable granules, dry fluids, aqueous fluids, dispersible wettable granules, emulsifiable concentrates and aqueous suspensions. Other suitable formulations are known for those skilled in the art.

Throughout the description and claims, the word "comprise" and its variants are not intended to exclude other technical features, additives, components or steps. To those skilled in the art, other objects, advantages and features of the invention will become apparent in part of the specification and practice of the invention. The following figures and examples are provided by way of illustration, and are not intended to be limiting of the present invention.

DESCRIPTION OF THE FIGURES

FIG. 4. Efficiency of treatments 1-5 with DSM 24682 (IAB/BS03) strain of *Bacillus subtilis* against the fungal disease *Bremia lactucae*, or lettuce mildew.

FIG. 5. Efficiency of treatments 6-10 with DSM 24682 (IAB/BS03) strain of *Bacillus subtilis* against the fungal disease *Bremia lactucae*, or lettuce mildew.

FIG. 6. Efficiency of treatments 11-15 with DSM 24682 (IAB/BS03) strain of *Bacillus subtilis* against the fungal disease *Bremia lactucae*, or lettuce mildew.

FIG. 7. A Efficiency of treatments 16-17 with DSM 24682 (IAB/BS03) strain of *Bacillus subtilis* against the fungal disease *Bremia lactucae*, or lettuce mildew. B. Additional data.

FIG. 8. A. B. Description of the study site.
FIG. 9. A. B. Description of the treatments.
FIG. 10. Assessment of the results.
FIG. 11. A. B. Description of the efficiencies.

BIBLIOGRAPHY

Schwinn et al., p. 244, Advances in plant pathology: *phytophthora infestans*, the cause of late blight of potato (Academic Press, San Diego, 1991)

Stabb et al., Applied Environ. Microbiol. 60: 4404-4412, 1990

Osburne et al., Am. Phytopathol. Soco 79(6), 1995

Smith et al. 1993

Plant Disease 77(2), 139-142

Leifert et al. (1995), J. Appl. Bacteriol. 78: 97-108, Astilbe

Sholberg et al. (1995), Can. J. Microbiol. 41: 247-252

Swinburne et al. (1975), Trans. Brit. Mycol. Soco 65: 211-217

Singh and Deverall (1984), Trans. Br. Mycol. Soco 83: 487-490

Ferreira et al. (1991), Phytopathology 81: 283-287)

Baker et al. (1983), Phytopathology 73: 1148-1152

Pusey et al. (1988), Plant Dis. 72: 622-626

McKeen et al. (1986), Phytopathology 76: 136-139

CRC Handbook of Antibiotic Compounds, Vol. I-XIV (CRC Press, Inc., Boca Ratón, Fla., 1980-87)

Bland et al. (1995), Proc. Plant Growth Regulation Soco Am. $22^{th}$: 105-107)

EXAMPLES

The following specific examples provided in this patent document illustrate the nature of the present invention. These examples are included for illustrative purposes only and are not to be interpreted as limitations to the invention claimed herein. Therefore, the examples described below illustrate the invention without limiting the scope thereof.

The examples given below validate and demonstrate that the subject matter being protected by the invention comprises:

- a characterized strain, and that this strain is unique and differentiable from others of the same species,
- that this strain has the ability to be a biological control agent, since, as seen in the in vitro assays, it presents activity against different pathogenic fungi.
- that this strain has an action spectrum different from other (as for example) QST 713 strain of *Bacillus subtilis*, as demonstrated in the assays carried out with lettuce, in order to fight *Bremia lactucae*, or lettuce mildew.
- the QST 713, as referred in ES2268774 and EP0981540B1 does not have an effect against *Bremia lactucae*, whereas the strain object of the present invention has. That shows a different action spectrum, and
- that the strain object of the present invention is up to 300 times more potent than QST 713 strain of *Bacillus subtilis*, given that as shown in the examples, it is capable of fighting said disease (*Bremia lactucae*), as a synthetic chemical product does (mancozeb+cymoxanil 4%), using a dose at least 300 times lower than the one used with the QST 713 strain.

Example 1. Complete Characterization of DSM 24682 (IAB/BS03) Strain

A "RiboPrint" analysis of DSM 24682 strain (IAB/BS03) strain has been performed, by using the EcoRI restriction enzyme, obtaining the following results:

A. The DSM 24682 (IAB/BS03) strain was identified as a *Bacillus subtilis* strain based on the DUP-12544 entry in DuPont Identification Library. Said pattern is based on DSM 449 strain.

Figure 1A:
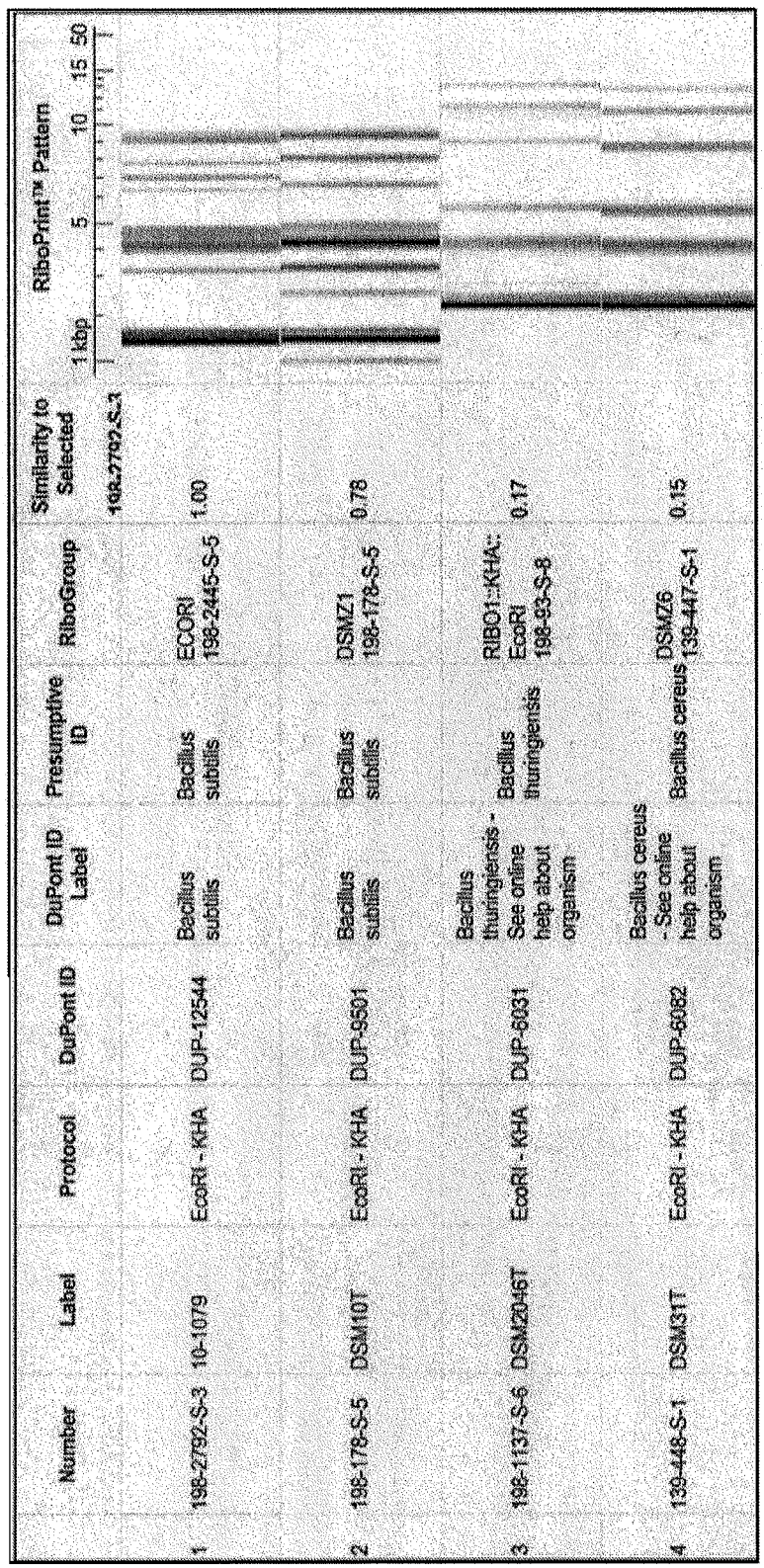
FIG. 1. A and B. Complete characterization of DSM 24682 (IAB/BS03) strain, wherein the differentiation of the particular *Bacillus subtilis* strain, against others such as *Bacillus thuringiensis* and *Bacillus cereus* is demonstrated.
Figure 1B:
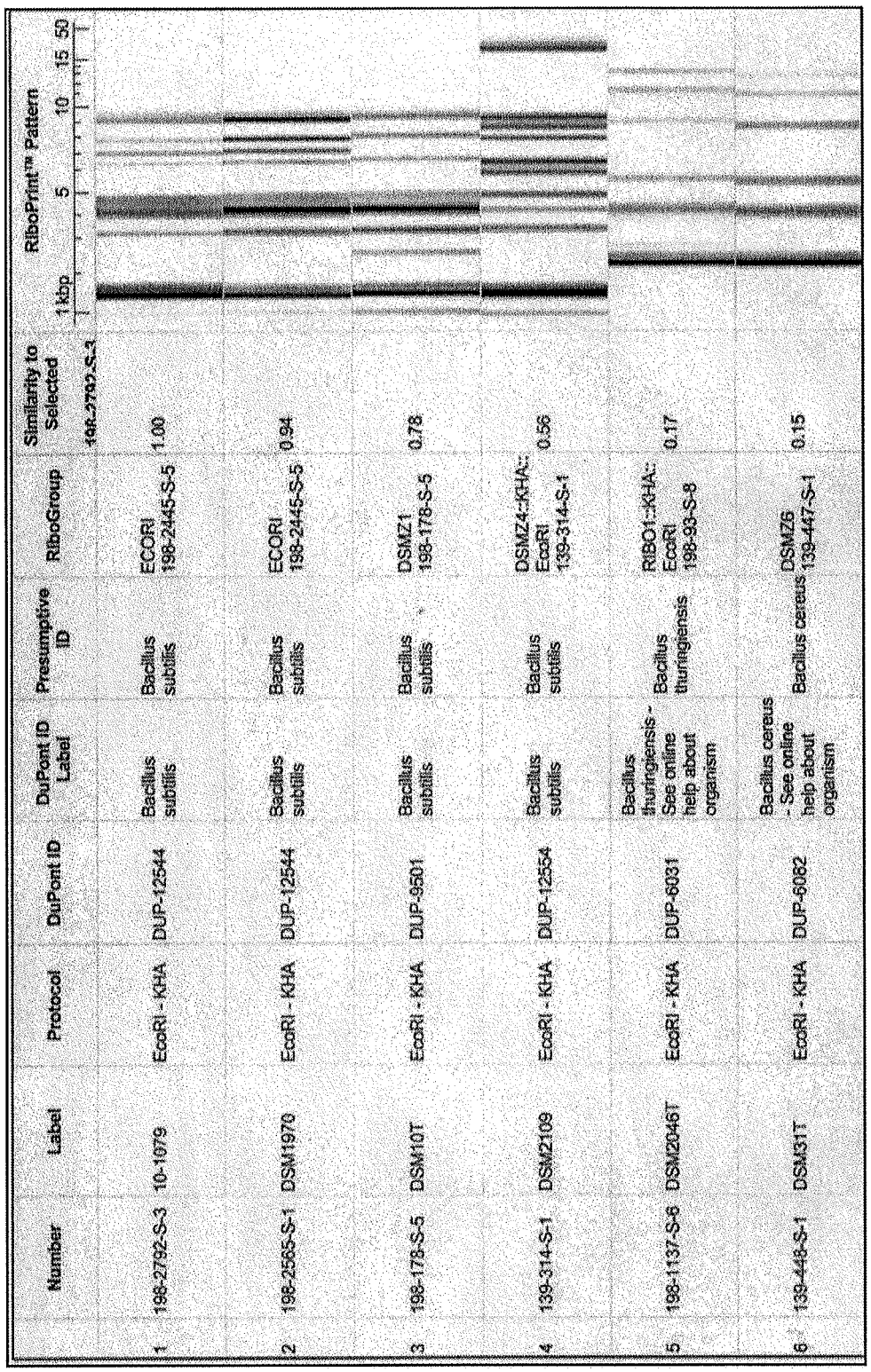

B. The pattern of DSM 24682 (IAB/BS03) strain differs significantly from patterns of other strain types such as *Bacillus thuringiensis* DSM $2046^T$ (only a 0.17 DuPont similarity index was obtained) and *Bacillus cereus* DSM $31^T$ (0.15 similarity index) (see FIG. 1 A). *Bacillus thuringiensis* and *Bacillus cereus* are not differentiable, based on the EcoRI patterns.

C. Therefore, with the intention of showing the diversity of the EcoRI patterns of *Bacillus subtilis*, the DSM $10^T$, DSM 1970 and DSM 2109 strains were included in the comparison assays (see FIG. 1 B). The pattern of the DSM 24682 (IAB/BS03) strain is clearly differentiated from said strains, since the following similarity indexes were obtained: 0.78 with respect to DSM $10^T$, 0.56 with respect to DSM 2109. However, it is similar to DSM 1970 strain, with an index of 0.94, and to DSM 449 strain, with an index of 0.94. DSM 24682 (IAB/BS03) and DSM 1970 strains share the same ECORI RiboGroup 198-2445-S-5, which shows that RiboPrinter is unable to detect differences between EcoRI patterns of both strains. In this example, the difference between EcoRI patterns of DSM 24682 (IAB/BS03) strain with respect to other *Bacillus subtilis* strains, except to DSM 1970 strain, with which DSM 24682 (IAB/BS03) strain shares the same RiboGroup ECORI 198-2445-s-5, is demonstrated.

Also, indicate that in the readings of the scannings of Example 1, the input number of DSM 24682 (IAB/BS03) strain is 10-1079, while the one of QST 713 band is 11-196.

Conclusion: Complete characterization of DSM 24682 (IAB/BS03) strain demonstrates the differentiation of said *Bacillus subtilis* particular strain, compared to others such as *Bacillus thuringiensis* and *Bacillus cereus*.

Example 2. Comparison of DSM 24682 (IAB/BS03) Strain Against QST 713 Strain

Figure 2:
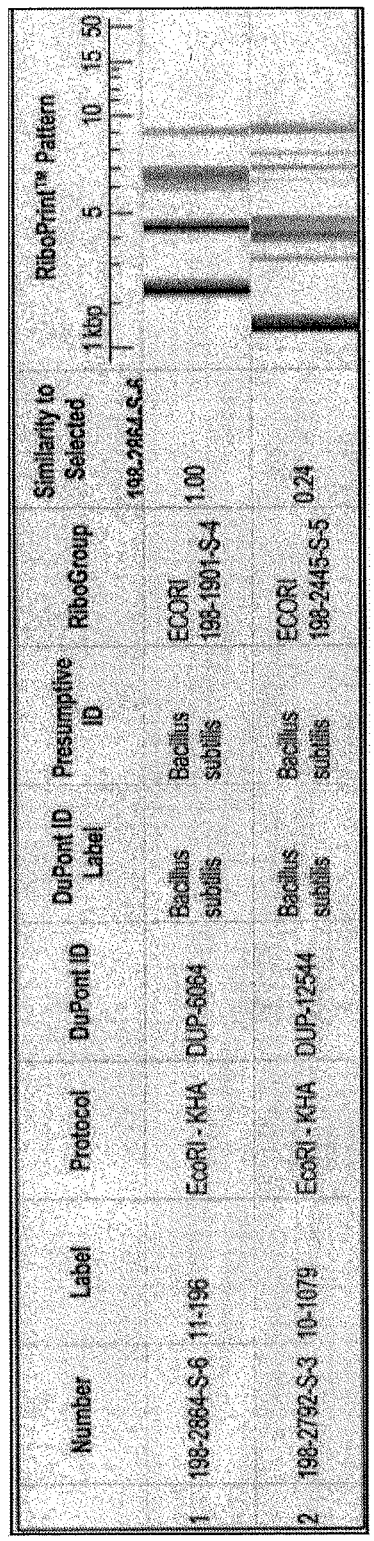
FIG. 2. Genetic profile of the DSM 24682 (IAB/BS03) strain compared to QST 713 strain, wherein it is specifically demonstrated that the existing similarity between both is just 0.24, and therefore, they are different *Bacillus subtilis* strains.

A genetic profile of DSM 24682 (IAB/BS03) strain was performed against QST 713 strain of *Bacillus subtilis*, wherein it is specifically demonstrated that the existing similarity between both strains is just 0.24, and therefore, they are different strains of *Bacillus subtilis*. Following the same method as described on Example 1, a 0.24 DuPont ID similarity index was obtained (see FIG. 2).

Conclusion: the genetic profile results demonstrate that the DSM 24682 (IAB/BS03) strain is a different strain from the QST 713 strain of *Bacillus subtilis*, as the DuPont ID similarity index obtained is just 0.24. For a better understanding to the readings of the scannings of Example 1, the input number of the DSM 24682 (IAB/BS03) strain is 10-1079, whereas in Example 2, the one of the band of QST 713 strain of *Bacillus subtilis* is 11-196.

Example 3. Study of the Activity of DSM 24682 (IAB/BS03) Strain Against Different Fungal Diseases In Vitro In order to determine if DSM 24682 (IAB/BS03) strain is effective in vitro against different laboratory-cultivable fungi, a series of in vitro assays were performed, in which it was evaluated the potential of the isolated DSM 24682 strain as biological control agent by studying its effects against the fungi *Alternaria solani*, *Botrytis cinerea*, *Fusarium oxysporum*, *Phytophthora* spp., *Rhizoctonia solani*, *Sclerotinia* spp. and *Verticillium* spp.

The qualitative measurement of the growth inhibition of different phytopathogenic fungi against DSM 24682 (IAB/BS03) strain of *Bacillus subtilis* was carried out during the assays. At each side of the PDA plates a DSM 24682 (IAB/BS03) *Bacillus subtilis* is seeded, and a pathogenic fungus is seeded in the centre. The plate is incubated for 7 to 14 days at 26° C., and both the fungus radial growth inhibition, in mm, compared to the control, and the antagonism %, are measured.

The results are detailed below (Table 1):

TABLE 1

| Microorganism | INHIBITION (mm) | Antagonism (%) |
|---|---|---|
| Alternaria | 10 | 67 |
| Botrytis | 10 | 94 |

TABLE 1-continued

| Microorganism | INHIBITION (mm) | Antagonism (%) |
|---|---|---|
| Fusarium | 5 | 60 |
| Phytophtora | 3 | 70 |
| Rhizoctonia | 6 | 24 |
| Sclerotinia | 6 | 37 |
| Verticillium | 9 | 42 |

Figure 3A:
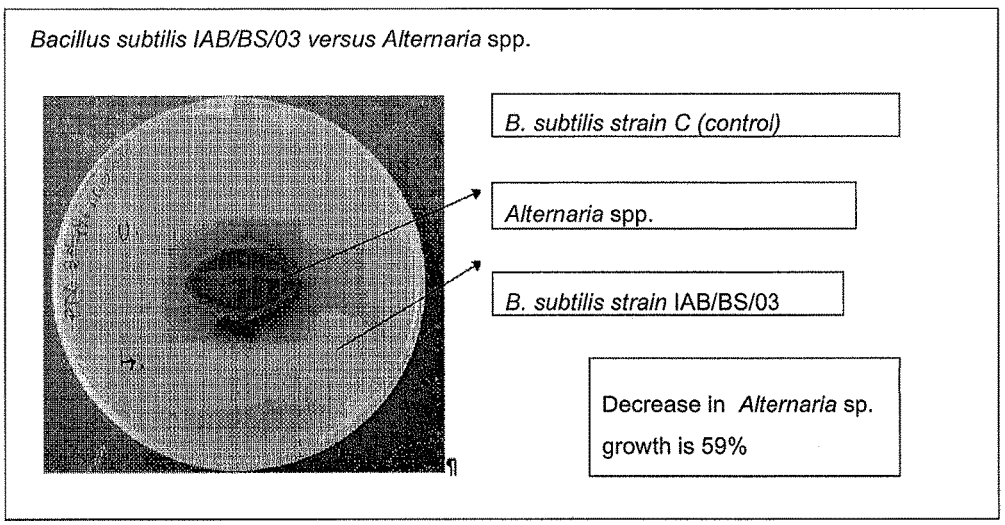
FIG. 3. A and B. Visual results of the fungicide effect of DSM 24682 (IAB/BS03) strain against *Alternaria* sp. and against *Fusarium oxysporum*, respectively. Specifically, the capacity of the DSM 24682 (IAB/BS03) strain to act as a biocontrol agent against *Alternaria* sp and *Fusarium oxysporum* is tested.
Figure 3B:
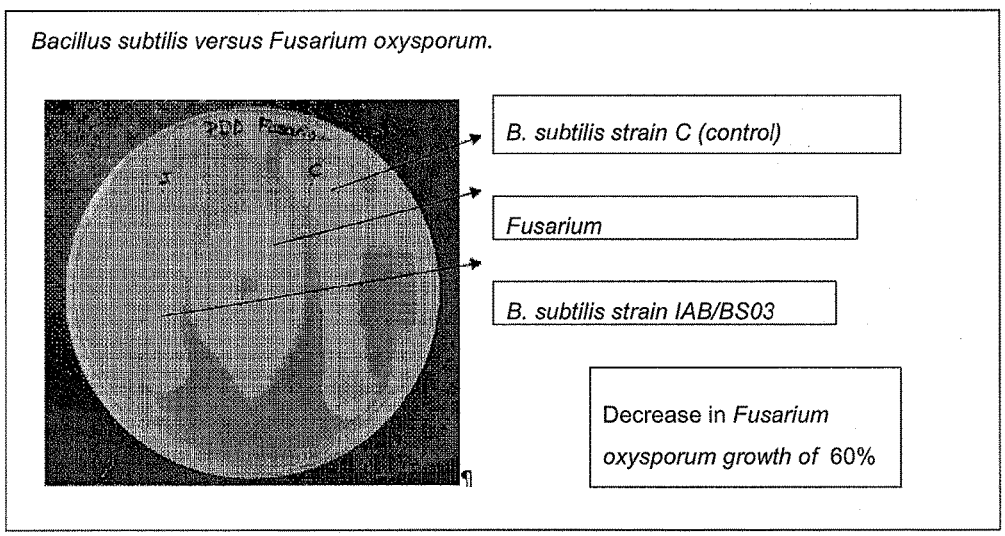

These results show that the DSM 24682 (IAB/BS03) strain of *Bacillus subtilis* produces antibiotics that inhibit the growth of different fungi, therefore being usable as biological control agent. The visual results of the effect against *Alternaria* sp. and against *Fusarium oxysporum* show that there is a decrease of 59% in *Alternaria* sp. growth, and of 60% of *Fusarium oxysporum* (see FIGS. 3A and 3B).

Conclusion: two types of inhibitory effect of DSM 24682 (IAB/BS03) strain of *Bacillus subtilis* against different fungi were found:

A direct antagonism against *Fusarium oxysporum* is produced, given that it was observed how in the contact zone, the fungi was unable to produce aerial mycelium.

The production of a fungal growth inhibitory substance against *Alternaria* sp. is also observed.

It is therefore concluded that the results show that the DSM 24682 (IAB/BS03) strain of *Bacillus subtilis* has a broad in vitro fungicide spectrum, and that both the complete broth and the supernatant could be used for this purpose, since the production of substances that inhibit the growth and development of different laboratory-cultivable fungi has been demonstrated.

Example 4. Analysis of the Activity of DSM 24682 (IAB/BS03) Strain of *Bacillus subtilis* Object of the Present Invention Against *Bremia lactucae* (Phytopathogenic Fungus) and Comparative with the Commercial Product QST 713 Strain of *Bacillus subtilis*

In patent EP 0 981 540 B1 it is indicated in paragraph 55, example 8, that the QST 713 strain (AQ713 strain) did not prevent against *Bremia lactucae*, or lettuce mildew, so the efficiency of treatments with the DSM 24682 strain of *Bacillus subtilis* against the fungal disease *Bremia lactucae* has been analyzed (see FIGS. 4-7)

Conclusion: the results show the effectiveness of treatments with DSM 24682 (IAB/BS03) strain of *Bacillus subtilis* object of the present invention against fungal diseases, such as *Bremia lactucae* or lettuce mildew, being those treatments equal to the chemical treatments employed, and obtaining a better result in terms of efficiency compared to another *Bacillus subtilis* strain (QST 713). The amount of inoculum needed in order to obtain the desired effects is considerably smaller and therefore, the DSM 24682 (IAB/BS03) strain of *Bacillus subtilis* is far more potent.

As an explanation and reference to the specific content of FIGS. 4-7, it is found by statistical processing that averages followed by the same letter do not differ significantly, and therefore, the treatments may be considered as having the same efficiency, except in column 8 of FIGS. 4, 5, 6 and 7, wherein the treatment based on the QST 713 strain, after 14 days of the last application, is significantly worse, and not comparable to the reference chemical treatment (CURZATE M).

In the referred example, the *Bacillus subtilis* (QST 713) with a microbial quality of $5.13 \times 10^{10}$ CFU/g was compared to the product formulated with the DSM 24682 (IAB/BS03)

strain, containing 2.04×10⁸ CFU/g (see attached analysis certificate, Table 2). The batch number used in the assay matches with the batch number of the certificate of analysis included in Table 2.

TABLE 2

Certificate of analysis of the product formulated with DSM 24682 (IAB/BS03) strain

| | |
|---|---|
| SAMPLE | *Bacillus subtilis* IAB/BS/03 WP formulation |
| BATCH | BS81101011 |
| *Bacillus subtilis* IAB/BS/03 CONTENT (¹) | 2.04 × 10⁸ CFU/g |
| INTERNAL CODE | 059/11/C |
| FORMULATION | WP |
| ANALYSIS DATE | 21$^{st}$ Jul. 2011 |

(¹) The amount of active ingredient was determined according to the validated analytical method described in the GLP study BT07711

This certifies that the application of the product with the DSM 24682 (IAB/BS03) strain object of the present invention, is carried out with a microbial quality at least 100 orders lower compared to the commercial product *Bacillus subtilis* QST 713 strain. If the doses used in each application are observed (reference in any one of the tables), it becomes apparent that the doses used for the product with the DSM 24682 strain object of the present invention have been from 100 g/100 L of water to 200 g/100 L of water, whereas the doses used for the commercial product *Bacillus subtilis* QST 713 strain have been of 600 g. That is to say, the doses used to apply the commercial product *Bacillus subtilis* QST 713 strain, as example of *B. subtilis* strain, is 3 times higher than the highest dose used for the application of the product with DSM 24682 (IAB/BS03) strain object of the present invention.

If the microbial quality is also taken on account, it can be stated that applying a dose 300 times lower of the product containing the DSM 24682 (IAB/BS03) strain object of the present invention, the control results of *Bremia lactucae* or lettuce mildew are significantly better 14 days after the last application. That is, that in comparison with the *Bacillus subtilis* QST 713 strain, the *Bacillus subtilis* IAB/BS03 strain is at least 300 times more potent and effective, regarding its retention of the antifungal effect on the plant.

We can therefore conclude that the DSM 24682 (IAB/BS03) strain object of the present invention is at least 300 times more potent than QST 713 strain, as a representative example of another specific strain of the same species (*Bacillus subtilis*). Furthermore, the DSM 24682 (IAB/BS03) strain object of the present invention has fungicide properties comparable to the treatment with mancozeb+ cymoxanil 4%, as representative example of a commercial chemical fungicide treatment.

Example 5. Determination of the Efficiency and Selectivity of the DSM 24682 (IAB/BS03) Strain of *Bacillus subtilis* Against the Brown Rot Disease in Stone Fruits in Order to Determine the Bactericide Effect of the Strain The efficiency and selectivity of the DSM 24682 (IAB/BS03) strain of *Bacillus subtilis* against the Brown Rot disease in stone fruit was determined using a microbial quality of 10⁸ CFU/g WP (see FIGS. 8-11). As with the previous assay, the microbial quality of the DSM 24682 (IAB/BS03) strain is lower (100 times lower in this case) than the effective dose of the commercial product *Bacillus subtilis* QST 713 strain. Tebuconazole (FOLICUR) is used in said assay.

Conclusion: in FIG. 11 the efficiency of the product containing the DSM 24682 (IAB/BS03) strain, object of the present invention, in the treatment of flowers and shoots against stone fruit trees Brown Rot bacterial disease (moniliasis) may be observed. Once the statistical analysis is carried out, efficiency percentages from 74.8 to 82.9% in flowers, and from 45.8 to 81.7% in shoots are observed. Furthermore, there are significant differences with respect to the control (untreated thesis), so the fungicidal as well as the bactericidal effect of the strain is demonstrated.

The invention claimed is:

1. A biologically pure culture of *Bacillus subtilis* IAB/BS03 strain deposited at the DSMZ German Type Culture Collection under Accession Number DSM 24682 in complete broth, wherein the strain presents antifungal and/or antibacterial activity.

2. The strain according to claim 1, which presents an action profile different from other *Bacillus subtilis* strains, and is at least 300 times more potent in terms of its capacity to act as a biological control agent in the field.

3. A composition comprising the strain described in claim 1 and a carrier, said composition having antifungal and antibacterial activity.

4. The composition according to claim 3, further comprising a chemical or biological pesticide.

5. A method for treatment and protection of plants and fruits against fungal and/or bacterial infections that comprises topically applying to the plants and fruits an effective amount of:
   a biologically active *Bacillus subtilis* IAB/BS03 strain deposited at the DSMZ German Type Culture Collection under Accession Number DSM 24682 in complete broth or
   a composition comprising the strain, and a carrier, or a chemical or biological pesticide.

6. The method according to claim 5, wherein the effective amount is 300 times lower than an effective amount of a different *Bacillus subtilis* strain in order to achieve the same fungicide potency as the different *Bacillus subtilis* strain.

7. The method according to claim 5, wherein the fungal and/or bacterial infections are caused by at least one microorganism selected from the group consisting of: *Alternaria* sp, *Botrytis* sp, *Fusarium* sp, *Phytophthora* sp, *Rhizoctonia* sp, *Sclerotinia* sp, *Verticillium* sp, *Leveillula* sp, *Venturia* sp, *Plasmopara* sp, *Uncinula* sp, *Pythium* sp, *Colletotrichum* sp, *Cladosporium* sp, *Monilinia* sp, *Acidovorax* sp, *Pseudomonas* sp, *Xanthomonas* sp, *Erwinia* sp, *Clavibacter* sp, *Sphaerotheca* sp and *Peronospora* sp.

8. The method according to claim 5, wherein the strain is applied as wettable powders, granules, fluids or microencapsulations.

9. The method according to claim 5, wherein the biologically active strain, or the composition, is topically applied at a location selected from the group consisting of: roots, leaves, flowers, fruits, a soil surrounding the roots, and a combination thereof.

\* \* \* \* \*